United States Patent
Prein et al.

(10) Patent No.: US 8,410,184 B2
(45) Date of Patent: Apr. 2, 2013

(54) REGENERATION OF ACIDIC ION EXCHANGERS

(75) Inventors: Michael Prein, Krefeld (DE); Christian Münnich, Leverkusen (DE); Ulrich Blaschke, Krefeld (DE)

(73) Assignee: Bayer MaterialScience AG (DE)

( * ) Notice: Subject to any disclaimer, the term of this patent is extended or adjusted under 35 U.S.C. 154(b) by 391 days.

(21) Appl. No.: 12/784,870

(22) Filed: May 21, 2010

(65) Prior Publication Data

US 2010/0305365 A1 Dec. 2, 2010

(30) Foreign Application Priority Data

May 30, 2009 (DE) .......................... 10 2009 023 551

(51) Int. Cl.
*B01J 38/60* (2006.01)
*B01J 38/62* (2006.01)

(52) U.S. Cl. ............... 521/26; 502/27; 502/28

(58) Field of Classification Search ............... 521/26; 502/27, 28
See application file for complete search history.

(56) References Cited

U.S. PATENT DOCUMENTS

| 3,037,052 | A | 5/1962 | Bortnick |
| 3,242,219 | A | 3/1966 | Farnham et al. |
| 4,051,079 | A * | 9/1977 | Melby .............................. 521/26 |
| 4,191,843 | A | 3/1980 | Kwantes et al. |
| 6,680,270 | B2 * | 1/2004 | Peemans et al. ................ 502/33 |
| 6,723,881 | B1 | 4/2004 | Bödiger et al. |

FOREIGN PATENT DOCUMENTS

| DE | 2727866 A1 | 12/1977 |
| DE | 19956229 A1 | 5/2001 |
| EP | 0324080 A1 | 7/1989 |
| GB | 842209 A | 7/1960 |
| GB | 849565 A | 9/1960 |
| GB | 883391 A | 11/1961 |
| WO | WO-01/37992 A1 | 5/2001 |

* cited by examiner

*Primary Examiner* — Joseph Kosack
*Assistant Examiner* — Matthew Coughlin
(74) *Attorney, Agent, or Firm* — Novak Druce Connolly Bove + Quigg LLP

(57) ABSTRACT

The invention relates to a method for regenerating acidic cation exchangers, which are used as catalysts in the reaction of phenols with aldehydes or ketones to give bisphenols, in particular to give bisphenol A, with acids, with the proviso that, in the method according to the invention, these cation exchangers experience very little mechanical damage due to swelling processes during the regeneration process.

14 Claims, No Drawings

REGENERATION OF ACIDIC ION EXCHANGERS

RELATED APPLICATIONS

This application claims benefit to German Patent Application No. 10 2009 023 551.5, filed May 30, 2009, which is incorporated herein by reference in its entirety for all useful purposes.

BACKGROUND OF THE INVENTION

The invention relates to a method for regenerating acidic cation exchangers, which are used, in particular as catalysts in the reaction of phenols with aldehydes or ketones to give bisphenols, in particular to give bisphenol A, with acids, with the proviso that, in the method according to the invention, these cation exchanger experience very little mechanical damage due to swelling processes during the regeneration process.

Condensation reactions of phenols with carbonyl compounds to give bisphenols with the use of acidic catalysts, in particular with the use of cation exchangers, are known (cf., for example, GB 842 209 A, GB 849 565 A or GB 883 391 A). It is also known that acidic cation exchangers which were deactivated by metal ions or were contaminated by organic by-products from the bisphenol preparation ("fouling") can be regenerated by suitable measures. Thus, for example, EP 324 080 A describes a method for regenerating acidic cation exchangers by treatment with bases and acids. However, the aspect of the mechanical intactness of the cation exchangers is not considered at all here and there is also no information as to how such an aim is to be achieved. Moreover, the sequence of the various washes of the ion exchanger with water, base and acid is so complicated in practice that it is unsuitable in practice for industrial production, in particular for regeneration in an existing plant.

The publication RD 369008 (Database Document Number) of "Research and Disclosure" (Derwent Publications Ltd., London, UK, Database Accession Number 1995-080031) also reports the regeneration of acidic cation exchangers, a complicated sequence of a plurality of treatments with different agents, such as water, ketone, base and acid being recommended, which sequence is unsuitable for a regeneration on the industrial scale in an existing continuously operating production plant, since too many foreign products have to be introduced into the production process and have to be strictly removed again. Here too, the consequences of mechanical damage to the cation exchanger by swelling processes is not considered.

DE 2 727 866 A1 describes a relatively simple sequence of washes with phenol, water and acid, dispensing with a wash with bases. However, here too no information is given concerning the swelling of the cation exchangers with water and the possible consequences of mechanical destruction. Information about the effects of the water concentration or about upper concentration limits of water in the wash medium phenol and water or phenol, water and acid on the properties of the ion exchanger treated in this manner is absent.

The prior art sets no defined upper limits of a reliable water concentration in the phenol-acid mixture in the regeneration, compliance with which makes it possible very substantially to avoid excessive swelling and hence bursting of the cation exchanger particle. On the contrary, according to the information in DE 2 727 866 A1, on page 8, the proportion of water for a successful regeneration of the ion exchanger bed may be up to 30% by weight. Under such conditions, however, there is a very considerable danger of excessive swelling of the cation exchanger with said consequences. Thus, the stated upper limit is not suitable for achieving the object presented here.

This aspect is of considerable importance since cation exchangers which are usually also deactivated by "fouling"—i.e. by incorporation of relatively high molecular weight condensates, for example of phenol and acetone, into the polymer network of the catalyst particle—may swell during the treatment with excessively high concentrations of water to such an extent that the osmotic pressure in the ion exchanger particle contaminated with these "fouling" components may be so high that it breaks. This results in the formation of fine fractions of the ion exchanger particle which, during operation in the intended manner, not only lead to blockage of fixed-bed reactors and filters but, in downstream process stages, can also give rise to major faults due to secondary reactions, with quality problems as a result thereof.

The cation exchangers are used as a rule as flow-through particle beds. The change in the overall particle size distribution of the cation exchanger due to particle fracture can furthermore adversely affect the pressure drop characteristic in the flow-through cation exchanger bed, which leads to a larger pressure drop in the bed and possible hydraulic limitations and hence limitations in the production quantities.

It was therefore the object to provide a technically simple and economical method for regenerating deactivated acidic cation exchangers, which leaves the particle structure of the ion exchanger particle substantially intact and converts the functional acidic groups, such as, for example, sulpho groups, bonded to the polymer matrix substantially back into their acidic form.

The avoidance of mechanical damage caused in this manner is of major importance because very fine fragments of particles of the cation exchanger can give rise to considerable problems, for example due to undesired secondary reaction, blockages of plant parts or pressure drop limitations, after the regeneration of said cationic exchanger and during the operation thereof in the intended manner. The method according to the invention is applied to acidic cation exchangers which are used as catalysts in chemical reactions and which, in the course of their use, have lost a part of their catalytic activity there, so that the conversion of the reaction is insufficient. By the method according to the invention for regenerating acidic cation exchangers, deactivated in this manner, with acids, the catalytic activity thereof is increased again so that economical reuse of these cation exchangers several times in chemical syntheses is permitted. Ion exchangers regenerated according to the invention are in particular acidic, optionally also modified cation exchangers which are used as catalysts in the reaction of phenols with aldehydes or ketones to give bisphenols, particularly to give bisphenol A. Modified cation exchangers are, for example, cation exchangers which, in addition to their function as cation exchangers by, for example, acidic groups, are treated by application of further chemically active components having additional functions. Such chemically active components may be, for example, cocatalysts which have, for example, inter alia thiol functions.

EMBODIMENTS OF THE INVENTION

An embodiment of the present invention is a method for regenerating a deactivated or partly deactivated acidic cation exchanger comprising washing an ion exchange catalyst taken out of operation with a mixture comprising phenol and acid, wherein the water content of said mixture is increased by the gradient method.

Yet another embodiment of the present invention is a method for regenerating a deactivated or partly deactivated acidic cation exchanger comprising a) washing an ion exchange catalyst bed with from 1 to 4 bed volumes (BV) of a mixture of phenol and acid;

b) washing said ion exchange catalyst bed with from 0.25 to 4 BV of a mixture of phenol and acid during which water is added to said mixture such that the water content of said mixture is increased by the gradient method from 0% by weight of water to 1% by weight of water;

c) washing said ion exchange catalyst bed with from 0.25 to 4 BV of a mixture of phenol and acid during which water is added to said mixture such that the water content of said mixture is increased by the gradient method from 1% by weight of water to 5% by weight of water;

d) washing said ion exchange catalyst bed with a mixture of phenol and from 5 to 25% by weight of water, until the electrical conductivity of said mixture is less than 50 µS/cm to obtain a washed ion exchange catalyst bed; and e) dewatering said washed ion exchange catalyst bed with phenol until the residual water content in the said phenol is less than 1% by weight;

wherein said ion exchange catalyst bed has been taken out of operation;

the acid content of the mixtures used in steps a), b), and c) is less than 10% by weight and greater than 0% by weight;

the BV corresponds to the volume of said ion exchange catalyst bed; and the temperature of said ion exchange catalyst bed is in the range of from 45° C. to 90° C.

Another embodiment of the present invention is the above method, wherein the acid content of the mixtures used in steps a), b), and c) is in the range of from 1% to 5% by weight.

Another embodiment of the present invention is the above method, wherein the temperature of said ion exchange catalyst bed is in the range of from 60° C. to 70° C.

Another embodiment of the present invention is the above method, wherein said ion exchange catalyst bed in step a) is washed with 2 bed volumes of said mixture.

Another embodiment of the present invention is the above method, wherein said ion exchange catalyst bed in step d) is washed with said mixture until the electrical conductivity of said mixture is less than 20 µS/cm.

Another embodiment of the present invention is the above method, wherein said ion exchange catalyst bed is in a reactor and said method is performed in said reactor.

Another embodiment of the present invention is the above method, wherein said acid is one or more Brönstedt acids having a pKa of less than 3.

Another embodiment of the present invention is the above method, wherein said acid is sulphuric acid, hydrochloric acid, nitric acid, phosphoric acid, perchloric acid, an aromatic sulphonic acid, a halogenated carboxylic acid, chloroacetic acid, trifluoroacetic acid, picric acid, citric acid, or a mixture thereof.

Another embodiment of the present invention is the above method, wherein the amount of said acid in said mixture does not exceed 20 mol %, based on the mixture of phenol and acid.

Another embodiment of the present invention is the above method, wherein the amount of said acid in said mixture is in the range of from 5 to 10 mol %, based on the mixture of phenol and acid.

Another embodiment of the present invention is the above method, wherein the amount of said acid in said mixture is in the range of from 1 to 5 mol %, based on the mixture of phenol and acid.

Another embodiment of the present invention is the above method, wherein said ion exchange catalyst bed was used to synthesize bisphenol.

Another embodiment of the present invention is the above method, wherein said ion exchange catalyst regenerated by said method is subsequently used to synthesize bisphenol.

DESCRIPTION OF THE INVENTION

Surprisingly, it has now been found that the object according to the invention is particularly efficiently achieved if deactivated or partly deactivated acidic cation exchangers are subjected to a regeneration process which comprises the following steps:

a) Washing an ion exchange catalyst taken out of operation with a mixture of phenol and acid, the content of acid in the phenol-acid mixture being less than 10% by weight and greater than 0% by weight, preferably 3-5% by weight. The temperature in the reactor bed flooded with the phenol-acid mixture goes from 45° C. to 90° C., preferably from 60° C. to 70° C. An amount of phenol-acid mixture is preferably 1 to 6 bed volumes, particularly preferably 2 to 4 bed volumes (BV), corresponding to the ion exchange catalyst bed in the reactor.

b) Increasing the water content by the gradient method in the phenol-acid mixture used for washing the ion exchange catalyst from 0% by weight of water to 1% by weight of water, the total volume of this mixture as wash solution preferably being 0.25 to 4 BV and increasing the water content by the gradient method in the phenol-acid mixture used for washing the ion exchange catalyst from 1% by weight of water to 5% by weight of water, the total volume of this mixture as wash solution preferably being 0.25 to 4 BV.

c) Washing the ion exchange catalyst with a mixture of phenol and water which preferably contains 5-25% by weight of water, until the electrical conductivity of the wash solution is less than 50 µS/cm, preferably less than 20 µS/cm.

d) Dewatering the correspondingly washed ion exchange catalyst with pure phenol, until the residual water content in the wash phenol is less than 1% by weight.

Increasing by the gradient method designates the increase of the content of a component in the solution which can be effected stepwise, linearly or nonlinearly. Preferably, the increase of the content of a component is carried out at a constant rate (e.g. +1% per BV wash solution).

The regeneration can take place either directly in the reactor or outside the reactor.

Preferably, the regeneration is carried out in the reactor.

Acidic cation exchangers in the context of the invention are, for example, ion exchangers which contain a partially crosslinked polystyrene, for example polystyrene crosslinked with divinylbenzene, as the polymer matrix, with degrees of crosslinking of 1 to 20%, preferably 1 to 10%, and which have sulpho groups chemically bonded to the polymer matrix in the H form (or acidic form). Typical sulphonic acid concentrations of the acidic cation exchangers are, for example, in the range from 3 to 7 mol/kg of dry mass of the cation exchanger. These ion exchangers may optionally contain further covalently or conically bonded cocatalysts in chemically bonded form; they are macroporous or gel-like, as described in U.S. Pat. No. 4,191,843 and U.S. Pat. No. 3,037,052, and have a finely divided spherical form.

Such acidic cation exchangers are important catalysts for the preparation of bisphenols from ketones or aldehydes and phenols. The acidic ion exchangers regenerated according to the invention are used, for example, as catalysts in the economically important preparation process for bisphenol A (BPA) from acetone and phenol. The ion exchangers used in such a process slowly lose their catalytic activity in the course of their use, in general after one or more years. Reasons for this deactivation are, for example:

ion exchange at the sulpho groups by metal ions which, for example, are introduced into the preparation process by the raw materials used. The resulting metal sulphonate groups are no longer catalytically active.

incorporation of relatively high molecular weight compounds into the polymer network of the ion exchanger particle; so-called "fouling". These relatively high molecular weight compounds, which may also assume a tar-like character, prevent access of the reactants to the active centres in the catalyst particle. They are substantially relatively high molecular weight condensates of phenol, bisphenol, acetone or acetone derivatives.

For example, steps of the regeneration process according to the invention comprise a) the treatment with acids, firstly the metal sulphonate groups (Me form) on the ion exchange resin being converted into sulpho groups (H form), and secondly the relatively high molecular weight "fouling" components described above undergoing acid cleavage to give low molecular weight constituents; and b) the treatment with defined amounts of water, following the acid treatment, in order to swell the ion exchanger particle as slowly and sufficiently as required, so that firstly the low molecular weight substances can be sufficiently washed out of the ion exchanger particle and the active centres can be exposed again, and that secondly mechanical damage to the cation exchanger particle is substantially ruled out.

The washing way of acid residues and the dewatering are already known treatment procedures on cation exchangers and are sufficiently well known to the person skilled in the art and are described, for example, in WO 2001037992 A1.

In a preferred embodiment, the ion exchange catalyst remains during the regeneration process in the reactor, which is taken out of operation. The acids and the water are preferably fed into the phenolic main stream via separate pipes and mixed in, for example, via static mixers. In another embodiment of the method according to the invention, the solutions are premixed in a separate vessel and fed to the cation exchanger to be regenerated. The outflowing wash liquids are removed from the customary preparation process and worked up separately.

The gentle regeneration of the cation exchanger can also be carried out outside the production reactor. For this purpose, the cation exchanger must be transferred from the reactor to a suitable regeneration vessel. The gentle regeneration of the cation exchanger can be carried out, for example, as a batch regeneration in apparatuses known to the person skilled in the art, for example stirred containers. In order to avoid mechanical damage to the cation exchanger, for example, gentle stirring and conveying units having a low shearing effect are advantageous.

In a preferred embodiment of the regeneration in the batch method, for example, a cation exchanger is stirred gently and under nitrogen in twice the volume of a mixture of phenol, sulphuric acid and water and the catalyst resin is then filtered off. The regeneration procedure can preferably be repeated several times, it being possible to vary the composition of the regeneration solution, in particular the water content. A particularly preferred embodiment of the regeneration in the batch method comprises repeating the regeneration three times, the water content of the regeneration solution being increased, for example, from 1% by weight through 3% by weight to 5% by weight, while the ratio of acid to phenol is kept constant.

After transfer, for example, to a column, the subsequent neutral wash is preferably effected with a mixture of phenol and water until a conductivity of <50 µS/cm, preferably <20 µS/cm, is measured in the outflow of the cation exchanger bed. The neutral wash, too, can be carried out batchwise, it being possible to vary the water content of the wash solution. Preferably, the water content of the neutral wash is of the same order of magnitude as the water content of the regeneration solution. The neutral wash can, however, also be carried out continuously after transfer to a column or to the reactor.

The dewatering of the cation exchanger bed can preferably be effected batchwise or, after transfer to a column or to the reactor, also continuously with phenol to a residual water content in the outflow of, preferably, 1%.

The acids preferably used in the regeneration process according to the invention are Brönstedt acids (proton-donating acids), preferably protic acids having a pKa of less than 3, such as, for example, mineral acids or strong organic acids. Particularly preferably used acids are inorganic acids, such as, for example: sulphuric acid, hydrochloric acid, nitric acid, phosphoric acid, perchloric acid, or organic acids, such as, for example, aromatic sulphonic acids, halogenated carboxylic acids, such as, for example, chloroacetic acid or trifluoroacetic acid, very acidic phenols, such as, for example, picric acid, or optionally also citric acid.

Sulphuric acid, hydrochloric acid and phosphoric acid are very particularly preferred. The concentration of these acids in the phenol should not exceed 20 mol %, based on the mixture of phenol and acid; preferred acid concentrations in the phenol are 5-10 mol %, particularly preferably 3-5 mol %, based on the mixture.

The amount of phenol-acid mixture which is required for regenerating a deactivated cation exchanger in step a) is at least a half bed volume (BV), based on the ion exchange catalyst bed in the reactor, not more than four times the BV, but preferably one to two BV, the BV being defined as the volume that the ion exchanger in the active, dewatered and phenol-containing H form occupies in a cylindrical reactor. If the cation exchanger is present, for example, as a catalyst bed in a continuously operated tubular reactor, the phenol-acid mixture is passed slowly through the catalyst bed to be regenerated, at a flow rate of preferably 1/10 to 2 BV per hour, in order to ensure a sufficient reaction time of the acid with the cation exchanger.

In a variant of the method according to the invention, the flow through of the cation exchanger bed is stopped from time to time in order to prolong the reaction time of the regeneration solution with components which deactivate the catalyst and are to be removed. The preferred additional reaction time is less than 24 h, particularly preferably 12 h or less.

The temperature in the catalyst bed of the reactor during the regeneration of the cation exchanger should not exceed 90° C., in order to avoid undesired secondary reactions; it should also not be below 45° C., in order to permit a sufficient reaction rate. The preferred temperatures are from 55° C. to 75° C.

The addition of water to the acidic wash solution is effected by the gradient method in order to avoid an excessively high water concentration in the wash solution. This is of considerable importance for a successful regeneration of the ion exchange resin since, in the case of excessively high water concentrations, there is the danger that the osmotic pressure in the ion exchanger particle will increase to such an extent that the rigid and inelastic particle contaminated with the "fouling" components will tear or break. This will result in the formation of fragments and fine fractions of the ion exchanger particle of the order of magnitude of μm, which can be filtered only in a complicated manner and, during normal operation of the cation exchanger as catalyst, can in this way enter subsequent process steps in which they can cause considerable problems due to undesired secondary reactions. Such fragments can also lead to blockage of filters and hence to impairment of the BPA preparation process during normal operation of the cation exchanger as a catalyst.

A change in the overall particle size distribution of the cation exchanger due to particle fracture can furthermore adversely affect the pressure drop characteristic in the flow-through cation exchanger bed, which can lead to a higher pressure drop in the bed and possible hydraulic limitations and hence limitations to production quantities.

The addition of water by the gradient method is effected, according to the invention, in such a way that, after the end of the washing of the cation exchanger with the phenol-acid mixture in a first downstream step, the concentration of water in this acidic phenol wash solution is increased from 0 to 1% by weight. Using such an acidic phenolic solution containing 0-1% by water of water, the cation exchanger is washed with an amount of 0.25 to 4 BV of this solution. Preferably, this washing is effected at a flow rate through the catalyst bed of ⅒ to 4 BV per hour. This is followed, in a second step, by an increase of the water concentration by the gradient method in the acidic phenolic wash solution from 1% by weight to 5% by weight. Using such an acidic phenolic solution containing 1-5% by weight of water, the cation exchanger is likewise washed with an amount of about one BV of this solution. Here too, this washing is preferably effected at a flow rate through the catalyst bed of ¼ BV per hour. By means of these measures, the maximum possible activation of the sulpho groups and the maximum possible decomposition of relatively high molecular weight condensates in the cation exchanger are achieved without mechanically damaging said cation exchanger.

After this increase in the water concentration by the gradient method in the acidic phenolic wash solution, excess acid and residues of cleavage products must be washed out as completely as possible from the polymer network of the cation exchanger, since they would otherwise interfere in the operation of the cation exchanger in the intended manner as a catalyst. This is effected by washing the cation exchanger with pure water or with a solution of phenol in water. Typical wash solutions contain 5-25% by weight of water in phenol. Here too, the preferred flow rate is ¼-2 BV per hour. The total amount of wash solution required depends on the electrical conductivity (μS/cm) of the wash solution flowing out of the catalyst bed. It is a measure of ionic impurities in the water. The methods of measurement are sufficiently well known to the person skilled in the art. This washing with water or phenol/water should be continued until the electrical conductivity falls below 50 μS/cm, preferably below 20 μS/cm. The temperature of the catalyst bed flooded with water or phenol/water should not exceed 80° C. and should not fall below 45° C.; wash temperatures in the range from 55° C. to 70° C. are preferred. The water used in particular in this washing should preferably be a demineralized water.

As a result of a relatively high water content in the neutral wash, the wash quantity is reduced but the risk of damage to the ion exchanger is increased. Considerable care is therefore advisable here. Furthermore, an increased wash throughput reduces the time requirement of the regeneration. In both cases, the reactor is more rapidly available again for production.

In a preferred embodiment, the cation exchanger thus regenerated and purified is activated for use as a catalyst in the bisphenol synthesis by, for example, substantially removing water from it. This dewatering is effected, for example, by washing the catalyst bed with pure phenol until the water content in the outflow of the purely phenolic wash solution from the catalyst bed is less than 1% by weight of water.

After this conditioning, the cation exchanger is available again as a catalyst, for example for bisphenol syntheses from ketones and phenols. The activity of a cation exchanger regenerated in this manner as a catalyst is such that the activity level of the new catalyst is virtually completely restored. The cation exchanger regenerated by the method according to the invention shows a catalyst deactivation rate which corresponds to that of the new catalyst in the industrial production process.

By repeating the method according to the invention for the catalyst regeneration several times if required, the total capacity of the cation exchanger can be slightly increased. However, a further positive influence on the catalyst activity is scarcely detectable.

The regeneration according to the invention is preferably effected on ion exchangers in fixed-bed reactors for condensation reactions, particularly preferably for the preparation of bis(4-hydroxyaryl)alkanes, very particularly preferably for the preparation of 2,2-bis(4-hydroxyphenyl)-propane (bisphenol A).

Suitable bis(4-hydroxyaryl)alkanes which are obtainable with the use of the ion exchanger as a catalyst are, for example, those of the general formula (I)

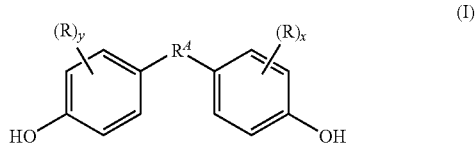

in which
$R^A$ represents a linear or branched $C_1$-$C_{18}$-alkylene radical, preferably $C_1$-$C_6$-alkylene radical, or a $C_5$-$C_{18}$-cycloalkylene radical, preferably a $C_5$-$C_{12}$-cycloalkylene radical,
R independently of one another represent a linear or branched $C_1$-$C_{18}$-alkyl radical, preferably $C_1$-$C_6$-alkyl radical, a $C_5$-$C_{18}$-cycloalkyl radical, preferably a $C_5$-$C_{12}$-cycloalkyl radical, a $C_6$-$C_{24}$-aryl radical, preferably a $C_6$-$C_{12}$-aryl radical, or a halogen radical and
x and y independently of one another represent 0 or an integer from 1 to 4, preferably independently of one another represent 0, 1 or 2.

Preferred bis(4-hydroxyaryl)alkanes are 2,2-bis(4-hydroxyphenyl)propane (bisphenol A (BPA)), 2,4-bis(4-hydroxyphenyl)-2-methylbutane, 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, 2,4-bis(3,5-dimethyl-4-hydroxyphenyl)-2-methylbutane, 1,1-bis(4-hydroxyphenyl)cyclohexane and 1,1-bis(4-hydroxyphenyl)-3,3,5-trimethylcyclohexane (bisphenol TMC).

Particularly preferred bis(4-hydroxyaryl)alkanes are 2,2-bis(4-hydroxyphenyl)propane (bisphenol A (BPA)), 2,2-bis(3,5-dimethyl-4-hydroxyphenyl)propane, 1,1-bis(4-hydroxyphenyl)cyclohexane and 1,1-bis(4-hydroxyphenyl)-3,3,5-trimethylcyclohexane (bisphenol TMC).

2,2-Bis(4-hydroxyphenyl)propane (bisphenol A) is very particularly preferred.

Bis(4-hydroxyaryl)alkanes are obtainable by processes known to the person skilled in the art by reacting aromatic monohydroxy compounds, which are not substituted in the p position with ketones which have at least one aliphatic group on the carbonyl function, in a condensation reaction. Preferably, an adduct of the bis(4-hydroxyaryl)alkane and the aromatic monohydroxy compound as starting material is obtained as an intermediate, which is then separated into the desired bis(4-hydroxyaryl)alkane and aromatic monohydroxy compound.

Suitable aromatic monohydroxy compounds are, for example, those of the general formula (II)

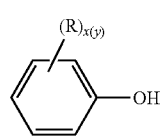

(II)

which are not substituted in the p position and in which

R independently of one another represent a linear or branched $C_1$-$C_{18}$-alkyl radical, preferably $C_1$-$C_6$-alkyl radical, a $C_5$-$C_{18}$-cycloalkyl radical, preferably a $C_5$-$C_{12}$-cycloalkyl radical, a $C_6$-$C_{24}$-aryl radical, preferably a $C_6$-$C_{12}$-aryl radical, or a halogen radical and X or y represents 0 or an integer from 1 to 4, preferably 0, 1 or 2.

Examples of suitable aromatic monohydroxy compounds of the general formula (II) are, for example, phenol, o- and m-cresol, 2,6-dimethylphenol, o-tert-butylphenol, 2-methyl-6-tert-butylphenol, o-cyclohexylphenol, o-phenylphenol, o-isopropylphenol, 2-methyl-6-cyclopentyl-phenol, o- and m-chlorophenol or 2,3,6-trimethylphenol. Phenol, o- and m-cresol, 2,6-dimethylphenol, o-tert-butylphenol and o-phenylphenol are preferred and phenol is very particularly preferred.

Suitable ketones are, for example, those of the general formula (III)

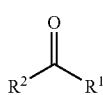

(III)

in which $R^1$ represents a linear or branched $C_1$-$C_{18}$-alkyl radical, preferably $C_1$-$C_6$-alkyl radical, and $R^2$ represents a linear or branched $C_1$-$C_{18}$-alkyl radical, preferably $C_1$-$C_6$-alkyl radical, or a $C_6$-$C_{24}$-aryl radical, preferably a $C_6$-$C_{12}$-aryl radical, or $R^1$ and $R^2$ together represent a linear or branched $C_4$-$C_{18}$-alkylene radical, preferably $C_4$-$C_{12}$-alkylene radical.

Examples of suitable ketones of the general formula (III) are acetone, methyl ethyl ketone, methyl propyl ketone, methyl isopropyl ketone, diethyl ketone, acetophenone, cyclohexanone, cyclopentanone, methyl-, dimethyl- and trimethylcyclohexanones, which may also have geminal methyl groups, e.g. 3,3-dimethyl-5-methylcyclohexanone (hydroisophorone). Preferred ketones are acetone, acetophenone, cyclohexanone and homologues thereof carrying methyl groups; acetone is particularly preferred.

$C_1$-$C_6$-Alkyl represents, for example, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-di-methylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, $C_1$-$C_{18}$-Alkyl moreover, for example, represents moreover, for example, represents n-heptyl and n-octyl, pinacyl, adamantyl, the isomeric menthyls, n-nonyl, n-decyl, n-dodecyl, n-tridecyl, n-tetradecyl, n-hexadecyl, n-octadecyl or stearyl.

$C_1$-$C_6$-Alkylene or $C_1$-$C_{18}$-Alkylene represents, for example, the alkylene groups corresponding to the preceding alkyl groups.

$C_5$-$C_{12}$-Cycloalkyl represents, for example, cyclopentyl, cyclohexyl, cyclooctyl or cyclododecyl.

Examples of $C_6$-$C_{24}$-Aryl or $C_6$-$C_{12}$-Aryl are phenyl, o-, p- or m-tolyl, naphthyl, phenanthrenyl, anthracenyl or fluorenyl.

Halogen may represent fluorine, chlorine, bromine or iodine, preferably fluorine or chlorine, particularly preferably chlorine.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

The catalyst regeneration was determined on the basis of three criteria:
 catalyst activity
 total capacity of the cation exchanger
 proportion of particle fragments before and after the regeneration Determination of the Catalyst Activity:

The catalyst activity was determined on the basis of the acetone conversion in a continuous-flow cation exchanger bed at a temperature of 60° C. and with the use of a cocatalyst, and a mercaptan derivative.

Determination of the Total Capacity:

The total capacity of the cation exchanger was determined according to DIN 54403.

Determination of the Proportion of Particle Fragments:

The proportion of particle fragments was determined by computer-aided statistical evaluation of optical micrographs.

Example 1

280 g of phenol-moist cation exchanger were washed into the column with the aid of phenol. "Phenol-moist cation exchanger" designates a cation exchanger whose water content is reduced by washing with phenol so that less than 1% by weight of water are measured in the outflow of the phenol wash. Thereafter, the supernatant phenol was discharged and the column was thermostated at 70° C. Approximately 1 BV of 5 wt.-% sulphuric acid in phenol (95 wt.-%) was added to the cation exchanger bed, so that the cation exchanger bed was completely covered by the acidic phenolic solution. The cation exchanger bed was treated with a mixture of 270 g of phenol and 15 g of concentrated sulphuric acid at a volume flow rate of about ¼ BV per hour, the proportion of water in the phenolic sulphuric acid having been increased linearly from 0% by weight to 1% by weight within 4 h. Thereafter, the cation exchanger bed was treated with a mixture of 270 g of phenol, 3 g of water and 15 g of concentrated sulphuric acid at a volume flow rate of about ¼ BV per hour, the proportion of water in the phenolic sulphuric acid having been increased linearly from 1% by weight to 5% by weight within the next 3 h.

The subsequent neutral wash was effected with a mixture of 95 parts of phenol and 5 parts of water at a volume flow rate of 0.7 BV per hour, the proportion of water in the wash solution having been increased to 3 parts of phenol and 1 part of water within 5 h, and washing was then effected until a conductivity of <20 µS/cm was measured in the outflow of the cation exchanger bed. The dewatering of the cation exchanger bed was effected with phenol up to a residual water content of 1% in the outflow.

Example 2

280 g of phenol-moist cation exchanger were washed into the column with the aid of phenol. Thereafter, the supernatant phenol was discharged and the column was thermostated at 70° C. Approximately 1 BV of 5 wt.-% sulphuric acid in phenol (95 wt.-%) was added to the cation exchanger bed, so that the cation exchanger bed was completely covered by the acidic phenolic solution. The cation exchanger bed was treated with a mixture of 270 g of phenol and 15 g of concentrated sulphuric acid at a volume flow rate of about ¼ BV per hour, the proportion of water in the phenolic sulphuric acid having been increased from 0% by weight to 1% by weight within 4 h. Thereafter, the cation exchanger bed was treated with a mixture of 270 g of phenol, 3 g of water and 15 g of concentrated sulphuric acid at a volume flow rate of about ¼ BV per hour, the proportion of water in the phenolic sulphuric acid having been increased from 1% by weight to 5% by weight within the next 3 h.

The subsequent neutral wash was effected with a mixture of 95 parts of phenol and 5 parts of water at a volume flow rate of 0.7 BV per hour until a conductivity of <20 µS/cm was measured in the outflow of the cation exchanger bed. The dewatering of the cation exchanger bed was effected with phenol up to a residual water content of 1% in the outflow.

Comparative Example 3

280 g of phenol-moist cation exchanger were washed into the column with the aid of phenol. Thereafter, the supernatant phenol was discharged and the column was thermostated at 70° C. The cation exchanger bed was treated with a mixture of 540 g of phenol, 30 g of water and 30 g of concentrated sulphuric acid at a volume flow rate of ¼ BV per hour.

The subsequent neutral wash was effected with a mixture of 3 parts of phenol and 1 part of water at a volume flow rate of 0.7 BV per hour until a conductivity of <20 µS/cm was measured in the outflow of the cation exchanger bed. The dewatering of the cation exchanger bed was effected with phenol up to a residual water content of 1% in the outflow.

Comparative Example 4

280 g of phenol-moist cation exchanger were washed into the column with the aid of phenol. Thereafter, the supernatant phenol was discharged and the column was thermostated at 70° C. The cation exchanger bed was treated in each case three times with a mixture of 540 g of phenol, 30 g of water and 30 g of concentrated sulphuric acid at a volume flow rate of ¼ BV per hour.

The subsequent neutral wash was effected with a mixture of 3 parts of phenol and 1 part of water at a volume flow rate of 0.7 BV per hour until a conductivity of <20 µS/cm was measured in the outflow of the cation exchanger bed. The dewatering of the cation exchanger bed was effected with phenol up to a residual water content of 1% in the outflow.

Comparative Example 5

280 g of phenol-moist cation exchanger were washed into the column with the aid of phenol. Thereafter, the supernatant phenol was discharged and the column was thermostated at 70° C. The cation exchanger bed was treated with a mixture of 570 g of phenol and 30 g of concentrated sulphuric acid at a volume flow rate of ¼ BV per hour.

The subsequent neutral wash was effected with a mixture of 96 parts of phenol and 4 parts of water at a volume flow rate of 0.7 BV per hour until a conductivity of <20 µS/cm was measured in the outflow of the cation exchanger bed. The dewatering of the cation exchanger bed was effected with phenol up to a residual water content of 1% in the outflow.

Comparative Example 6

280 g of phenol-moist cation exchanger were washed into the column with the aid of phenol. Thereafter, the supernatant phenol was discharged and the column was thermostated at 70° C. The cation exchanger bed was treated with a mixture of 540 g of phenol, 30 g of water and 30 g of concentrated sulphuric acid at a volume flow rate of ¼ BV per hour.

The subsequent neutral wash was effected with a mixture of 3 parts of phenol and 1 part of water at a volume flow rate of 0.7 BV per hour until a conductivity of <20 µS/cm was measured in the outflow of the cation exchanger bed. The dewatering of the cation exchanger bed was effected with phenol up to a residual water content of 1% in the outflow.

Comparative Example 7

280 g of phenol-moist cation exchanger were washed into the column with the aid of phenol. Thereafter, the supernatant phenol was discharged and the column was thermostated at 70° C. The cation exchanger bed was treated with a mixture of 540 g of phenol, 30 g of water and 30 g of concentrated sulphuric acid at a volume flow rate of ¼ BV per hour.

The subsequent neutral wash was effected with a mixture of 95 parts of phenol and 5 parts of water at a volume flow rate of 0.7 BV per hour until a conductivity of <200/cm was measured in the outflow of the cation exchanger bed. The dewatering of the cation exchanger bed was effected with phenol up to a residual water content of 1% in the outflow.

Comparative Example 8

280 g of phenol-moist cation exchanger were washed into the column with the aid of phenol. Thereafter, the phenol was completely discharged, the cation exchanger bed was treated with a mixture of 270 g of phenol, 15 g of water and 15 g of concentrated sulphuric acid and the column was thermostated at 70° C. The cation exchanger bed was then treated with a mixture of 270 g of phenol, 15 g of water and 15 g of concentrated sulphuric acid at a volume flow rate of ¼ BV per hour.

The subsequent neutral wash was effected with a mixture of 95 parts of phenol and 5 parts of water at a volume flow rate of 0.7 BV per hour until a conductivity of <20 μS/cm was measured in the outflow of the cation exchanger bed. The dewatering of the cation exchanger bed was effected with phenol up to a residual water content of 1% in the outflow.

Example 9

The cation exchanger regenerated according to Example 1 by the method according to the invention was tested in a long-term test of more than 3600 h at a temperature of 60° C. in a flow-through cation exchanger bed. The low deactivation rate found corresponds to that of the new cation exchanger.

| Example | Acetone conversion before regeneration [%] | Acetone conversion after regeneration [%] | Total capacity before regeneration [mol/kg] | Total capacity after regeneration [mol/kg] | Delta proportion of fragments [%] | Total time of the regeneration [h] |
|---|---|---|---|---|---|---|
| 1 | 62.7 | 84.5 | 3.8 | 4.38 | 27 | 41 |
| 2 | 62.7 | 84.3 | 3.8 | 4.35 | 23 | 47 |
| 3 * | 62.7 | 84.8 | 3.8 | 4.4 | 47 | 43 |
| 4 * | 62.7 | 84.0 | 3.8 | 4.4 |  | 59 |
| 5 * | 58.4 | 66.9 | 3.28 | 3.64 |  | 54 |
| 6 * |  |  |  |  | 47 | 43 |
| 7 * |  |  |  |  | 34.5 | 48 |
| 8 * | 62.7 | 83.7 | 3.2 | 4.3 |  | 43 |

* Comparative Example

The invention claimed is:

1. A method for regenerating a deactivated or partly deactivated acidic cation exchanger comprising washing an ion exchange catalyst taken out of operation with a mixture comprising phenol and acid, wherein the water content of said mixture is increased by the gradient method.

2. A method for regenerating a deactivated or partly deactivated acidic cation exchanger comprising
    a) washing an ion exchange catalyst bed with from 1 to 4 bed volumes (BV) of a mixture of phenol and acid;
    b) washing said ion exchange catalyst bed with from 0.25 to 4 BV of a mixture of phenol and acid during which water is added to said mixture such that the water content of said mixture is increased by the gradient method from 0% by weight of water to 1% by weight of water;
    c) washing said ion exchange catalyst bed with from 0.25 to 4 BV of a mixture of phenol and acid during which water is added to said mixture such that the water content of said mixture is increased by the gradient method from 1% by weight of water to 5% by weight of water;
    d) washing said ion exchange catalyst bed with a mixture of phenol and from 5 to 25% by weight of water, until the electrical conductivity of said mixture is less than 50 μS/cm to obtain a washed ion exchange catalyst bed; and
    e) dewatering said washed ion exchange catalyst bed with phenol until the residual water content in the said phenol is less than 1% by weight;
    wherein
        said ion exchange catalyst bed has been taken out of operation;
        the acid content of the mixtures used in steps a), b), and c) is less than 10% by weight and greater than 0% by weight;
        the BV corresponds to the volume of said ion exchange catalyst bed; and
        the temperature of said ion exchange catalyst bed is in the range of from 45° C. to 90° C.

3. The method of claim 2, wherein the acid content of the mixtures used in steps a), b), and c) is in the range of from 1% to 5% by weight.

4. The method of claim 2, wherein the temperature of said ion exchange catalyst bed is in the range of from 60° C. to 70° C.

5. The method of claim 2, wherein said ion exchange catalyst bed in step a) is washed with 2 bed volumes of said mixture.

6. The method of claim 2, wherein said ion exchange catalyst bed in step d) is washed with said mixture until the electrical conductivity of said mixture is less than 20 μS/cm.

7. The method of claim 2, wherein said ion exchange catalyst bed is in a reactor and said method is performed in said reactor.

8. The method of claim 2, wherein at least one of the acids from step a, b, or c is one or more Brönstedt acids having a pKa of less than 3.

9. The method of claim 7, wherein the at least one acid is sulphuric acid, hydrochloric acid, nitric acid, phosphoric acid, perchloric acid, an aromatic sulphonic acid, a halogenated carboxylic acid, chloroacetic acid, trifluoroacetic acid, picric acid, citric acid, or a mixture thereof.

10. The method of claim 2, wherein the amount of at least one of the acids from step a, b, or c in the mixture from step a, b, or c does not exceed 20 mol %, based on the mixture of phenol and acid.

11. The method of claim 9, wherein the amount of the at least one acid in the mixture from step a, b, or c is in the range of from 5 to 10 mol %, based on the mixture of phenol and acid.

12. The method of claim 10, wherein the amount of the at least one acid in the mixture from step a, b, or c is in the range of from 1 to 5 mol %, based on the mixture of phenol and acid.

13. The method of claim 2, wherein said ion exchange catalyst bed was used to synthesize bisphenol.

14. The method of claim 2, wherein said ion exchange catalyst regenerated by said method is subsequently used to synthesize bisphenol.

* * * * *